United States Patent [19]

Gazzani

[11] Patent Number: 4,889,843

[45] Date of Patent: Dec. 26, 1989

[54] SALT OF TRISACCHARIDE, AND COMPOSITION AND PROCESS FOR RE-STIMULATING HAIR GROWTH

[75] Inventor: Giovanni Gazzani, Appiano Gentile, Italy

[73] Assignee: Crinos Industria Farmacobiologica Spa., Villa Guardia, Italy

[21] Appl. No.: 298,213

[22] Filed: Jan. 17, 1989

Related U.S. Application Data

[63] Continuation of Ser. No. 916,881, Oct. 9, 1986, abandoned.

[30] Foreign Application Priority Data

Oct. 10, 1985 [IT] Italy .................................. 22424 A/85

[51] Int. Cl.$^4$ ........................ C08B 37/08; A61K 7/06; A61K 35/00
[52] U.S. Cl. ........................................ 514/54; 536/54; 536/122; 536/123; 514/256; 514/880
[58] Field of Search .......................... 514/54, 880, 256; 536/54, 122, 123

[56] References Cited

U.S. PATENT DOCUMENTS

| | | | |
|---|---|---|---|
| 3,832,340 | 8/1974 | Wirth | 536/54 |
| 3,887,703 | 6/1975 | Manoussos et al. | 514/880 |
| 4,139,619 | 2/1979 | Chidsey, III | 514/237 |
| 4,736,024 | 4/1988 | Della Valle et al. | 536/54 |

FOREIGN PATENT DOCUMENTS

| | | | |
|---|---|---|---|
| 0662580 | 2/1965 | Belgium | 514/54 |
| 0035919 | 9/1981 | European Pat. Off. | 514/880 |
| 0107885 | 5/1984 | European Pat. Off. | . |
| 0182756 | 5/1986 | European Pat. Off. | . |
| 0188793 | 7/1986 | European Pat. Off. | 514/880 |
| 57-102811 | 6/1982 | Japan | 424/195.1 |
| 1098935 | 1/1968 | United Kingdom | . |
| 8302558 | of 0000 | World Int. Prop. O. | . |
| 0002558 | 8/1983 | World Int. Prop. O. | . |

OTHER PUBLICATIONS

Chemical Abstracts, vol. 99, No. 12, Sep. 1983, p. 334, Abstract No. 93515d, Columbus, Ohio, U.S.; & JP-A-58 88 306 (T. Kaneko) 26-05-83.

Chemical Abstracts, vol. 100, No. 18, Apr. 1984, p. 351, Abstract No. 14482e, Columbus, Ohio, U.S.; and JP-A-59 07 109 (Lion Corp.) 14-01-1984.

*Primary Examiner*—Ronald W. Griffin
*Assistant Examiner*—Nancy S. Carson
*Attorney, Agent, or Firm*—McAulay Fisher Nissen & Goldberg

[57] ABSTRACT

The salt formed between the polyanions forming the Trichosaccharide and the $NH_2$ groups of 2,4-diamino-6-piperidino-pyrimidine-3-oxide represents a novel trichogenic factor by which the activity of the single components is enhanced and the seriously toxic side effects of Minoxidil are done away with.

8 Claims, No Drawings

SALT OF TRISACCHARIDE, AND COMPOSITION AND PROCESS FOR RE-STIMULATING HAIR GROWTH

This application is a continuation of application Ser. No. 916,881, filed Oct. 9, 1986, now abandoned.

The present invention relates to a novel compound having trichogenic action, obtained through salification of Trichosaccharide with Minoxidil. Trichosaccharide consists of a natural mixture of glycosaminoglycan sulfates and polydeoxyribonucleotides extracted from animal organs rich with connective tissue.

Trichosaccharide has shown both in the animal and in the human being a definite and well detectable stimulating activity, trophic with respect to the piliferous follicles. In the human being, moreover antidandruff and sebum regulating action can be revealed.

As a matter of fact the hair regrowth activity of Trichosaccharide is disclosed for instance in UK Pat. No. 1098935, to which reference is made from more details, both with respect to activity and preparation and purification. It has been used as the active ingredient of hair treatment compositions known under the trade marks FOLTENE and, more recently, VITACRIN T.

Moreover Trichosaccharide was firstly discovered and studied for human therapy. More particularly, Trichosaccharide was studied for the treatment of atherosclerosis, alternations of the lipidic metabolism and peripheral arteriopathies, and is the active ingredient of drugs (like Ateroid) still in use since early sixties.

U.S. Pat. No. 3,887,703 to which reference is herein made, discloses the detailed method of preparation, this method being still in use today.

The prevailing feature of Trichosaccharide in the hair treatment is the exclusively local activity thereof, namely restricted to the application area whereby systemic effects and toxicity are absent. Such a feature which can be attributed to its origin is also explained with the relevant affinity thereof for the treated cutaneous areas, whereby for a long period of time, it is retained in the application zone.

In turn 2,4-diamino-6-piperidino-pyrimidine-3-oxide, also known as Minoxidil having the formula:

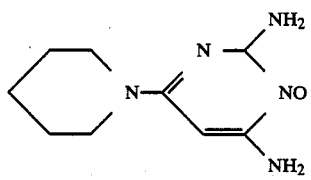

has been used chemically for a number of years in the treatment of the essential hypertension, and among the side effects detected in the patients treated with this drug there are sluggishness and hypertrichosis.

Recently the use of Minoxidil has been described in the prevention or therapy, treatment of baldness, as well as the treatment of several forms of human alopecia.

The results thus obtained indicate an anti-baldness activity for this drug, the use of which is however seriously limited due to the possible secondary toxic effects disclosed in the literature and, because of the possibility of inducing sluggishness and hypertrichosis in women who, in view of these masculinizing effects, are prevented from the use thereof. In a surprising manner it has been found that the salt obtained between the polyanions forming Trichosaccharide and the NH$_2$ groups being part of the molecule of Minoxidil constitutes a novel trichogenic factor, by which the activity of the single component is enhanced. It is to be particularly pointed out that with this novel salt the dreadful secondary toxic effects of Minoxidil can be avoided.

Without it being an undue limitation, it seems plausible as an explanation according to which these results of relevant interest are achieved since Trichosaccharide, by retaining the Minoxidil in its place of application, permits definitely lower dosages to be used, without any reduction of efficaciousness, avoiding any systemic effect and permitting the use thereof also for women who shall no longer be afraid of the growing of evident hair in the areas in which they must be absent for the female sex (face, arms, legs, breast, etc.).

The preparation of the salt according to the present invention takes place by reacting in a water-alcohol solvent mixture Trichosaccharide, preferable freshly obtained from a solution of a salt thereof, e.g. sodium salt, with Minoxidil, also in the form of a solution. The resulting salt contains Trichosaccharide and Minoxidil in the ratio of 1:1 to 1:0.25, depending on the starting Trichosaccharide.

The following example detailedly illustrates the preparation process of the salt of the present invention.

10 g of Trichosaccharide in form of sodium salt with a content of Na$^+$ ions of 7% are dissolved in water to a volume of 1000 ml and the resulting solution is passed through a column (2 cm diameter, 50 cm height), containing 150 ml of Anberlite IR 120 (in form H$^+$) resin.

The operation must be carried out at 4° C. to preserve the SO$_3$H groups. The resin is washed with 200 ml of water and the combined eluates are added with 200 ml of a 3.5% alcoholic solution of Minoxidil dissolved in a water-alcohol solution at 50° alcoholic degrees.

The salt of Trichosaccharide and Minoxidil is obtained wherein the two products are contained in the ratio of 1:0.68.

At the end of the salification the reaction mixture is concentrated under reduced pressure, the temperature being maintained below 50° C., and then lyophilized to obtain the salt of Trichosaccharide and Minoxidil in the dry state.

The thus obtained salt has been analytically tested (I.R. spectra and diffractometer analysis, besides the elemental analysis).

The IR spectra of the novel salt in comparison with those of Trichosaccharide sodium salt confirm the different structures of these two substances.

In turn the diffractometer analysis has been carried out on samples of:
(1) Minoxidil
(2) Trichosaccharide sodium salt (about 7% Na$^+$)
(3) salt of Trichosaccharide with Minoxidil.

The sample (1) appears well crystallized, whereas the samples (2) and (3) are of amorphous nature, although each having a peak different from that of the other.

At the elemental analysis for the salt of the present invention the following values have been found:
C% 37.87; H% 5.61; N% 15.25.

The preliminary toxicological tests show that by intraperitoneal route Minoxidil has an acute toxicity expressed as LD$_{50}$ of about 250 mg/kg, whereas in the case of the novel salt of the present invention are LD$_{50}$ of about 380 mg/kg i.p. is found.

In order to assess the properties of the salt of Trichosaccharide with Minoxidil according to the invention a test of hair stimulating activity has been carried out by an injecting route in the reddish Burgundy rabbit. To this end 5 reddish rabbits, weighing 5±0.5 kg, normally fed and stalled, have been shaved in the back area with an electric razor.

The day after the shaving, and after having checked the absence of irritated parts, the skin area thus prepared was marked with fourteen points corresponding in pairs to the sides of the vertebral column.

In the marked points intradermic injections have been made in double for a mutual control.

On the whole in the five tested animals seven double tests have been carried out.

The injections have been carried out once a day for two weeks in the same point, for a total of ten treatments (saturday and sunday being excluded).

The results of the observations carried out after 15 and 30 days are reported in the table 1.

TABLE 1

| Tested compounds | RABBITS | | | | | | | | | |
|---|---|---|---|---|---|---|---|---|---|---|
| | A | | B | | C | | D | | E | |
| | after day | | | | | | | | | |
| | 15 | 30 | 15 | 30 | 15 | 30 | 15 | 30 | 15 | 30 |
| Placebo | − | − | − | − | − | − | − | − | − | − |
| 5% Minoxidil | − | +− | − | − | + | +− | − | − | +− | − |
| 1.9% salt of Trichosaccharide with Minoxidil (1:0.9) | ++ | +++ | ++ | ++ | + | ++ | +++ | +++ | ++ | +++ |
| 1% Trichosaccharide | + | ++ | ++ | +++ | +++ | + | ++ | ++ | + | ++ |
| 2% Minoxidil | − | +− | + | + | +− | + | − | +− | − | +− |
| 0.5% Minoxidil | +− | + | +− | +− | − | − | +− | − | − | − |
| 0.25% Minoxidil | − | − | − | +− | − | +− | − | − | − | +− | wherein
− = no regrowth
+− = doubtful regrowth
+ = evident regrowth
++ = mean regrowth
+++ = abundant regrowth From the above table it is clearly demonstrated that Trichosaccharide stimulates the hair regrowth and that in turn Minoxidil gives doubtful results, independent from the administered dose.

Lastly the salt of Trichosaccharide with Minoxidil causes the hair regrowth to be abundantly stimulated, thus evidencing a synergistic action. Same examples of formulations based on the novel salt according to the invention are now given for illustrative but non limiting purpose.

EXAMPLE 1

Hair lotions

| (a) salt of Trichosaccharide and Minoxidil (1:0.9) | 1.9% |
|---|---|
| propylene glycol | 3.0% |
| ethyl alcohol | 12.0% |
| preservants | enough |
| distilled water | up to 100% |
| (b) Salt of Trichosaccharide and Minoxidil (1:0.45) | 1.45% |
| propylene glycol | 3.00% |
| ethyl alcohol | 12.00% |
| preservants | enough |
| distilled water | up to 100% |
| (c) Salt of Trichosaccharide and Minoxidil (1:0.25) | 1.25% |
| propylene glycol | 3.00% |
| ethyl alcohol | 12.00% |
| preservants | enough |

-continued

| distilled water | up to 100% |
|---|---|

EXAMPLE 2

Beard regrowth stimulating lotion

| Salt of Trichosaccharide and Minoxidil (1:0.9) | 1.9% |
|---|---|
| propylene glycol | 5.0% |
| ethyl alcohol | 25.0% |
| preservants | enough |
| distilled water | up to 100% |

It is finally pointed out that other types of formulations, both as regards the recipe and as regards the presence of other components possibly endowed with different activity, are possible and foreseable falling within the scope of the present invention.

What is claimed is:

1. A salt of trichosaccharide with 2,4-diamino-6-piperidino-pyrimidine-3-oxide, the ratio of trichosaccharide to the 2,4-diamino-6-piperidino-pyrimidine-3-oxide being between 1:1 and 1:0.25.

2. The salt of claim 1 wherein the ratio is 1:0.9.

3. A composition for restimulating hair growth comprising a hair restimulating effective amount of the salt of claim 1, propylene glycol, ethyl alcohol, and preservants.

4. A composition for restimulating hair growth comprising a hair restimulating effective amount of the salt of claim 2, propylene glycol, ethyl alcohol, and preservants.

5. A method for restimulating hair growth on a portion of the body comprising treating the body portion with a hair growth restimulating effective amount of the salt of claim 1, said treatment being carried out at least once per day for a sufficient number of days to restimulate hair growth.

6. A method for restimulating hair growth on a portion of the body comprising treating the body portion with a hair growth restimulating effective amount of the salt of claim 2, said treatment being carried out at least once per day for a sufficient number of days to restimulate hair growth.

7. The method of claim 5, wherein the hair to be restimulated is beard hair.

8. The method of claim 6, wherein the hair to be restimulated is beard hair.

* * * * *